(12) United States Patent  
Surti (10) Patent No.: US 8,267,857 B2  
(45) Date of Patent: Sep. 18, 2012

(54) EXPANDABLE PORT FOR ACCESSING A BODILY OPENING

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 275 days.

(21) Appl. No.: 12/696,203

(22) Filed: Jan. 29, 2010

(65) Prior Publication Data

US 2010/0204549 A1  Aug. 12, 2010

Related U.S. Application Data

(60) Provisional application No. 61/148,576, filed on Jan. 30, 2009.

(51) Int. Cl.
*A61B 1/32* (2006.01)
(52) U.S. Cl. ........................................ 600/203; 600/206
(58) Field of Classification Search .......... 600/201–246; 606/191, 197–200, 153
See application file for complete search history.

(56) References Cited

U.S. PATENT DOCUMENTS

| | | | | |
|---|---|---|---|---|
| 2,313,164 A * | 3/1943 | Nelson | ........................... | 600/208 |
| 4,562,832 A * | 1/1986 | Wilder et al. | ................. | 600/223 |
| 5,025,778 A | 6/1991 | Silverstein et al. | | |
| 5,197,971 A | 3/1993 | Bonutti | | |
| 5,279,565 A * | 1/1994 | Klein et al. | ................... | 604/105 |
| 5,281,225 A * | 1/1994 | Vicenzi | ............................ | 606/62 |
| 5,707,355 A | 1/1998 | Zimmon | | |
| 5,882,345 A | 3/1999 | Yoon | | |
| 5,947,896 A * | 9/1999 | Sherts et al. | ................... | 600/229 |
| 6,080,182 A | 6/2000 | Shaw et al. | | |
| 6,083,154 A * | 7/2000 | Liu et al. | ........................ | 600/234 |
| 6,315,733 B1 | 11/2001 | Zimmon | | |
| 6,371,968 B1 * | 4/2002 | Kogasaka et al. | ............. | 606/190 |
| 6,488,692 B1 | 12/2002 | Spence et al. | | |
| 6,551,270 B1 | 4/2003 | Bimbo et al. | | |
| 6,652,492 B1 | 11/2003 | Bell et al. | | |
| 6,689,062 B1 | 2/2004 | Mesallum | | |
| 6,932,764 B2 * | 8/2005 | Kashyap | ........................ | 600/210 |
| 7,717,847 B2 | 5/2010 | Smith | | |

(Continued)

FOREIGN PATENT DOCUMENTS

CA 2724111 A1 11/2009

(Continued)

OTHER PUBLICATIONS

PCT International Search Report/Written Opinion for PCT/US2010/022572.

(Continued)

*Primary Examiner* — Eduardo C Robert
*Assistant Examiner* — Lynnsy Schneider
(74) *Attorney, Agent, or Firm* — Brinks Hofer Gilson & Lione (57) ABSTRACT

Medical systems, devices and methods are provided for accessing a bodily opening. One embodiment of a medical device generally includes a flexible sheath and an expandable member. The flexible sheath has a length suitable for forming the pathway along a longitudinal axis. The expandable member is connected to a distal portion of a sheath. The expandable member is operable between a collapsed configuration and an expanded configuration. The expandable member includes a plurality of longitudinally extending struts connected together by a wire frame. The plurality of struts move radially and circumferentially relative to one another between collapsed and expanded configurations.

21 Claims, 8 Drawing Sheets

U.S. PATENT DOCUMENTS

| | | |
|---|---|---|
| 7,785,251 B2 | 8/2010 | Wilk |
| 7,785,333 B2 | 8/2010 | Miyamoto et al. |
| 7,798,998 B2 | 9/2010 | Thompson et al. |
| 7,815,589 B2 | 10/2010 | Meade et al. |
| 7,815,591 B2 | 10/2010 | Levine et al. |
| 7,819,836 B2 | 10/2010 | Levine et al. |
| 2002/0022764 A1 | 2/2002 | Smith et al. |
| 2002/0193806 A1 | 12/2002 | Moenning et al. |
| 2003/0093104 A1 | 5/2003 | Bonner et al. |
| 2003/0233109 A1 | 12/2003 | Green |
| 2004/0073242 A1 | 4/2004 | Chanduszko |
| 2005/0056292 A1 | 3/2005 | Cooper |
| 2006/0135984 A1 | 6/2006 | Kramer et al. |
| 2006/0135985 A1 | 6/2006 | Cox et al. |
| 2006/0161187 A1* | 7/2006 | Levine et al. .................. 606/153 |
| 2006/0200004 A1 | 9/2006 | Wilk |
| 2006/0211919 A1 | 9/2006 | Wilk |
| 2006/0212063 A1 | 9/2006 | Wilk |
| 2006/0224183 A1 | 10/2006 | Freudenthal |
| 2006/0229653 A1 | 10/2006 | Wilk |
| 2006/0241344 A1 | 10/2006 | Wilk |
| 2006/0241480 A1 | 10/2006 | Wilk |
| 2006/0241570 A1 | 10/2006 | Wilk |
| 2006/0241651 A1 | 10/2006 | Wilk |
| 2006/0252997 A1 | 11/2006 | Wilk |
| 2006/0253123 A1 | 11/2006 | Wilk |
| 2007/0123840 A1 | 5/2007 | Cox |
| 2007/0135803 A1 | 6/2007 | Belson |
| 2007/0163596 A1 | 7/2007 | Mikkaichi et al. |
| 2008/0021277 A1 | 1/2008 | Stefanchik et al. |
| 2008/0039786 A1 | 2/2008 | Epstein et al. |
| 2008/0058650 A1* | 3/2008 | Saadat et al. .................. 600/478 |
| 2008/0249474 A1 | 10/2008 | Baker |
| 2008/0287743 A1 | 11/2008 | Smith et al. |
| 2009/0112062 A1 | 4/2009 | Bakos |
| 2009/0143643 A1 | 6/2009 | Weitzner et al. |
| 2009/0149714 A1 | 6/2009 | Bonadio |
| 2009/0276055 A1 | 11/2009 | Harris et al. |
| 2010/0010303 A1 | 1/2010 | Bakos |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0114033 A1 | 5/2010 | Fischvogt |
| 2010/0168522 A1 | 7/2010 | Wenchell et al. |
| 2010/0249525 A1 | 9/2010 | Shelton, IV et al. |
| 2010/0256636 A1 | 10/2010 | Fernandez et al. |
| 2010/0261962 A1 | 10/2010 | Friedberg |
| 2010/0261974 A1 | 10/2010 | Shelton, IV et al. |
| 2010/0261975 A1 | 10/2010 | Huey et al. |
| 2010/0262080 A1 | 10/2010 | Shelton, IV et al. |
| 2010/0268162 A1 | 10/2010 | Shelton, IV et al. |
| 2010/0268253 A1 | 10/2010 | Ahlberg et al. |
| 2010/0286483 A1 | 11/2010 | Bettuchi et al. |
| 2011/0009704 A1 | 1/2011 | Marczyk et al. |

FOREIGN PATENT DOCUMENTS

| | | |
|---|---|---|
| EP | 1985226 A2 | 10/2008 |
| WO | WO 98/50104 | 11/1998 |
| WO | WO 2005/023358 A1 | 3/2005 |
| WO | WO 2006/029370 A2 | 3/2006 |
| WO | WO 2007/019117 A1 | 2/2007 |
| WO | WO 2007/038715 A1 | 4/2007 |
| WO | WO 2009/140594 A2 | 11/2009 |

OTHER PUBLICATIONS

PCT International Search Report/Written Opinion for PCT/US2009/044143.

PCT International Preliminary Report on Patentability for PCT/US2009/044143.

PCT International Search Report/Written Opinion for PCT/US2010/056721.

PCT International Search Report/Written Opinion for PCT/US2009/036173.

PCT Amendments Under Article 34 for PCT/US2009/036173.

PCT Supplemental Amendments Under Article 34 for PCT/US2009/036173.

* cited by examiner

EXPANDABLE PORT FOR ACCESSING A BODILY OPENING

CROSS-REFERENCE TO RELATED APPLICATIONS

This application claims the benefit of U.S. Provisional Application Ser. No. 61/148,576 filed on Jan. 30, 2009, entitled "EXPANDABLE PORT FOR ACCESSING A BODILY OPENING" the entire contents of which are incorporated herein by reference.

FIELD OF THE INVENTION

The present invention relates generally to medical systems, devices and methods to access a bodily opening via a bodily lumen, such as an opening in a wall of the gastrointestinal tract, for deployment of an endoscope and/or other medical devices.

BACKGROUND OF THE INVENTION

Openings in bodily walls may be formed to gain access to adjacent structures of the body, such techniques being commonly referred to as translumenal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies, tubal ligations, or other operations, all in a minimally invasive manner. Many translumenal procedures for gaining access to various body cavities using other bodily lumens have also been developed. For example, the bodily lumens of the gastrointestinal tract are often endoscopically explored and can be utilized to provide access to the peritoneal cavity and other body cavities. U.S. patent application Ser. No. 12/025,985 filed Feb. 5, 2008, discloses such a procedure, and is incorporated herein by reference in its entirety.

Although translumenal procedures are minimally invasive, there are also various risks involved. For example, when an opening is formed in a bodily wall of the gastrointestinal tract, such as in the stomach or intestines, spillage of the stomach contents, intestinal contents or other bodily fluids into the adjacent body cavity can occur. Travel of bacteria laden fluids outside of the gastrointestinal tract may cause unwanted and sometimes deadly infection. Traditional overtubes have been used to protect the mouth and esophagus while delivering an endoscope to the stomach. However, these overtubes do not seal to the gastric wall. Furthermore, traditional overtubes are quite rigid and can restrict the ability to manipulate the endoscope as desired.

BRIEF SUMMARY OF THE INVENTION

The present invention provides medical systems, devices and methods for accessing a bodily opening that are, among other things, safe and reliable, and that aid in the manipulation of the endoscope or other medical tool. One embodiment of a medical device for forming a pathway from an external orifice to a bodily opening defined by tissue of an internal bodily lumen is provided in accordance with the teachings of the present invention. The medical device generally includes a flexible sheath and an expandable member. The flexible sheath has a length suitable for forming the pathway along a longitudinal axis. The expandable member is connected to a distal portion of a sheath. The expandable member is operable between a collapsed configuration and an expanded configuration. The expandable member includes a plurality of longitudinally extending struts connected together by a frame. The plurality of struts move radially and circumferentially relative to one another between collapsed and expanded configurations.

According to more detailed aspects, each strut is pivotally attached to the frame. Each strut has distal and proximal ends that flare radially outwardly. Each strut preferably has a length about equal to or greater than about 3 mm. The frame preferably includes one or more frame members forming a serpentine shape, wherein the plurality of struts are attached to spaced apart apexes of the serpentine shape.

According to still further detailed aspects, the medical device preferably also includes an elongated accessory tube defining an accessory lumen. The distal end of the accessory tube is attached to the expandable member. Accessory tube is preferably sized in the range of 3 French to 40 French. The accessory tube is connected to a strut. A strut may define a connection ringlet sized to receive the accessory tube. The sheath may be connected to any portion of the expandable member. In one embodiment, the sheath may be connected at a radial position outside of the accessory tube, wherein the accessory tube passes through an opening in the sheath and extends along the exterior of the sheath.

A suture may be connected to the plurality of struts in a manner such that proximal retraction of the suture relative to the plurality of struts causes the expandable member to take its collapsed configuration. Each strut preferably includes a bore formed therein and sized to receive the suture. The suture is fixedly connected to at least one of the plurality of steps and slideably connected to the remainder of the struts. A plurality of struts define a port in the expanded configuration that is sized to receive an endoscope therethrough. The sheath is collapsible over a substantial portion of its length and operable between a collapsed configuration and an expanded configuration.

A method for accessing a bodily opening defined by tissue of an internal bodily lumen via an external orifice is also provided in accordance with the teachings of the present invention. The method includes the step of providing a medical device comprising a flexible sheath and an expandable member such as those described above. The distal end of the sheath and the expandable member are delivered within the perforation while the expandable member is in its collapsed configuration. The expandable member is operated to its expanded configuration such that the plurality of struts form a port within the interior of the perforation of the bodily wall.

According to more detailed aspects, when the medical device includes an elongated accessory tube, the method further includes the steps of passing a first instrument through the port formed by the expandable member and passing a second instrument through the accessory lumen. A surgical procedure may be performed using both the first and second instruments. When the expandable member includes a suture for controlling operation between configurations, the method may include the step of maintaining tension on the suture during delivery and then releasing tension to operate the expandable member to is expanded configuration. Further, the suture may be proximally retracted to collapse the expandable member and the medical device may be proximally withdrawn.

DETAILED DESCRIPTION OF THE INVENTION

In the present application, the term "proximal" refers to a direction that is generally towards a physician during a medical procedure, while the term "distal" refers to a direction that is generally towards a target site within a patient's anatomy during a medical procedure.

Turning now to the figures, FIGS. 1-4 depict a medical device 20 for forming a pathway from an external orifice to a bodily opening defined by tissue of an internal bodily lumen, constructed in accordance with the teachings of the present invention. As is known in the art, the external orifice typically is a natural orifice such as the mouth, anus, vagina, ears, nose, etc., although it will be recognized by those skilled in the art that the medical device 20 may also be employed through intentionally formed orifices such as those made during laparoscopic or similar procedures. Similarly, the bodily opening defined by the tissue of an internal bodily lumen may be intentionally formed or may be naturally occurring, and the internal bodily lumen may comprise a portion of the gastrointestinal tract or any other internal bodily lumen, as will be recognized by those skilled in the art.

The medical device 20 generally comprises an expandable member 22 and a flexible sheath 24. The flexible sheath 24 generally extends from a proximal portion 26 to a distal portion 28 and has a length suitable for forming the pathway, i.e. its length is sized depending upon the particular orifice and bodily lumen being traversed. The sheath 24 defines a sheath lumen 30 (FIG. 5) through which an endoscope 100 (FIG. 11) or other medical instrument may be traversed for accessing the bodily opening. Likewise, the expandable member 22 defines a port 32 through which the endoscope 100 or other medical instrument may pass.

Figure 1:
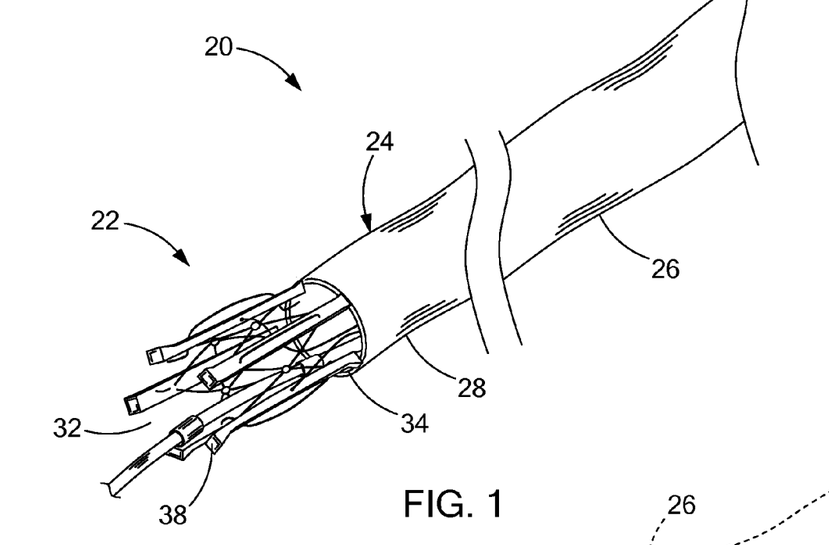
FIG. 1 is a perspective view of a medical device constructed in accordance with the teachings of the present invention.
Figure 2:
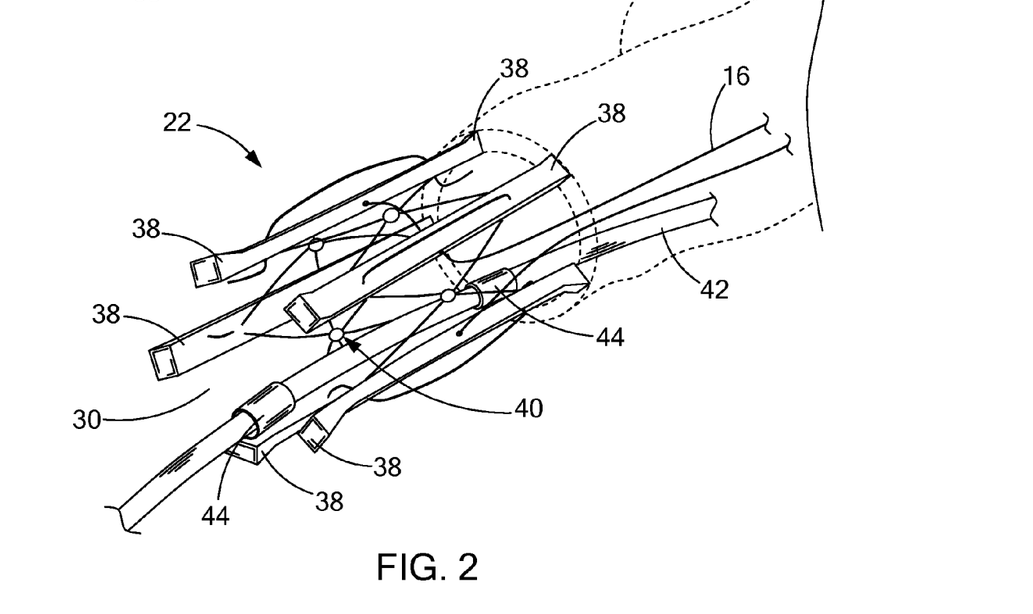
FIG. 2 is a perspective view of an expandable member forming a portion of the medical device depicted in FIG. 1.

The expandable member 22 is connected to the distal portion 28 of the sheath 24, and more particularly a proximal end 34 of the expandable member 22 is connected to the distal end of the flexible sheath 24. As best seen in FIG. 2, the expandable member 22 generally includes a plurality of struts 38 connected to a wire frame 40. Generally, the expandable member 22 is operable between a collapsed configuration, shown in FIG. 3, in an expanded configuration shown in FIG. 2. The plurality of struts 38 are circumferentially spaced apart in an annular configuration and connected to the wire frame 40. The wire frame 40 enables the plurality of struts 38 to move radially and circumferentially relative to one another between the collapsed and expanded configurations. The proximal and distal ends of each strut 38 preferably include a flange 56 or other structure which extends radially outwardly to facilitate retaining the expandable member 22 within the perforation or other bodily opening.

An accessory tube 42 is also connected to the expandable member 22. In the depicted embodiment, one of the struts 38 defines two ringlets 44 which are sized to receive the accessory tube 42 therein and connect the tube 42 to the expandable member 22. The accessory tube 42 defines an accessory lumen through which various medical devices may be deployed to facilitate procedures and accessorize another instrument (such as the endoscope 100) pass through the sheath 24 and port 32 defined by the expandable member 22. Preferably the accessory tube 42 has a diameter from about 3 French to about 40 French.

Figure 4:
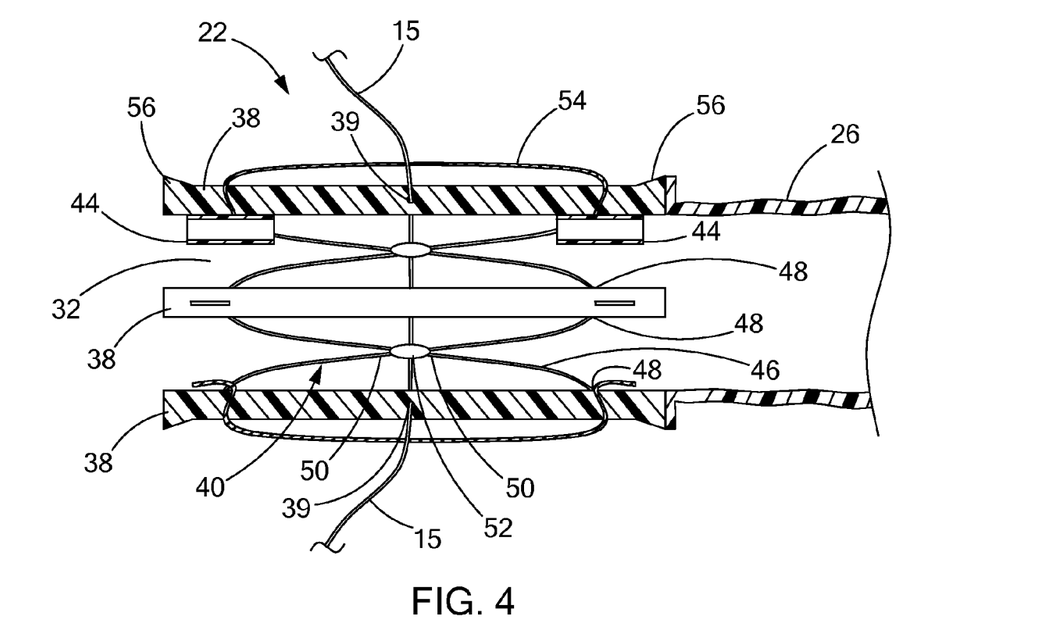
FIG. 4 is a cross-sectional view of the expandable member of FIG. 2.

As best seen in FIG. 4, each strut 38 extends longitudinally to define the proximal and distal ends 34, 36 of the expandable member 22. Each strut 38 preferably has a length about 3 mm or greater, and most preferably about 10 mm. The wire frame 40 generally includes at least one wire 46 which is bent into a V-shape having spaced apart ends 48 which are connected to adjacent struts 38. The wire frame 40 is connected to each strut 38 by simply embedding the wires 46 into the struts 38, although known attachment methods may be used including molding, bonding (e.g. heat bonding), adhesives, friction fits or mechanical features may be employed. Each V-shape may be formed by a single wire 46, or a single wire 46 may be formed into a zig-zag shape to define a plurality of alternating V-shapes. Although the frame 40 has been described and shown has being comprised of one or more wires defining V-shapes, it will be recognized by those skilled in the art that the frame 40 may be formed out of other materials and structures, for example as is known in the stent art. By way of example, a frame or stent may be formed from a canula that is laser cut to define one or more rows of serpentine bends (e.g. U-shaped or sinusoidal), and thus the frame members may be unitarily formed or separately formed and later joined using known methods. Materials such as metals, alloys, plastics and the like may also be employed to form the frame 40.

Figure 3:
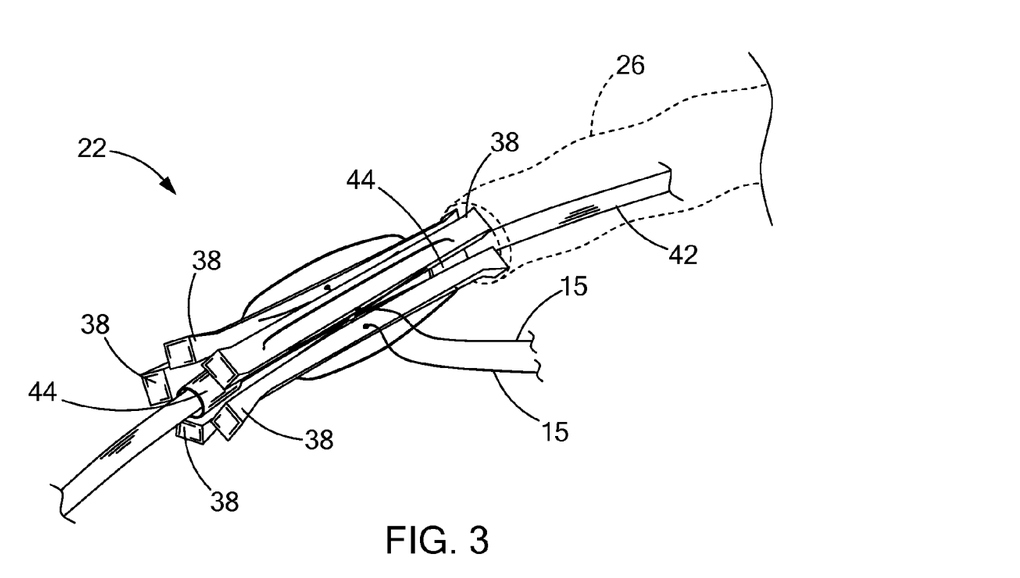
FIG. 3 is a perspective view of the expandable member of FIG. 2 in a different configuration.

As shown in FIG. 4, the wire frame 40 preferably includes two series of alternating V-shapes formed by wires 46 that are spaced longitudinally. The apexes 50 of the adjacent wires 46 may be connected by a bead 52, such as a weld or other connection member known to be suitable for connecting elements of a wire frame. However, it will also be recognized that the struts 38 can serve to interconnect the wires 46, and thus the beads 52 may not be needed. By connecting the plurality of struts 38 to the spaced apart ends 48 of the V-shaped wires 46, bending or folding of the wires 46 allow the struts 38 to move relative to one another and move between the expanded configuration of FIG. 2 and collapsed configuration (FIG. 3). In particular, the ends 48 of the V-shaped wires 46 are pivotally connected to the struts 38, such as by allowing the wires 46 to pass through the struts 38. It will also be noted that the expandable member 22 may include a plurality of exterior wires 54 connected to the plurality of struts 38 and extending along the exterior thereof. The exterior wires 54 may facilitate engaging the tissue of the perforation or other bodily opening.

It can also be seen in FIG. 4 that each strut 38 includes a transverse bore 39 formed therein and sized to slidably receive a suture 15 therethrough. The suture 15 is fixedly connected to at least one of the struts 38, and is slidably connected to the bore 39 to the remainder of the struts 38.

Proximal retraction of the suture 15 relative to the struts 38 causes the expandable member 22 to take its collapsed configuration shown in FIG. 3.

Figure 5:
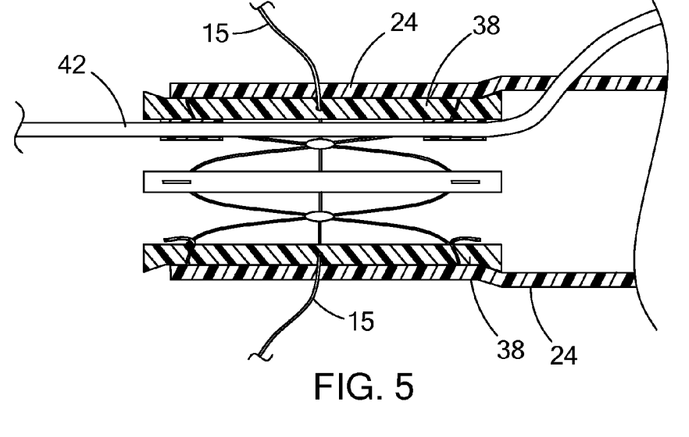
FIG. 5 is a cross-sectional view of an alternate embodiment of the medical device depicted in FIG. 1.
Figure 6:
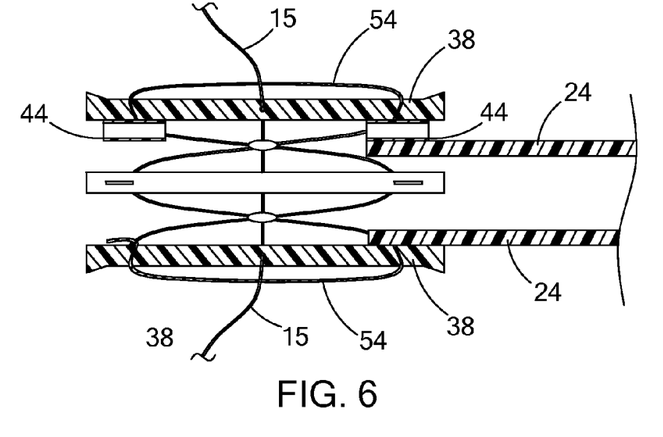
FIG. 6 is a cross-sectional view of another alternate embodiment of the medical device depicted in FIG. 1.

It will be recognized that the flexible sheath 24 may be connected to the expandable member 22 at any point along its length in various manners. The flexible sheath 24 and struts 38 of the expandable member 22 are both preferably formed of plastics, as discussed in further detail below, and thus may be connected using conventional methods such as heat bonding, mechanical bonding, adhesives, fasteners, suturing or the like. In the embodiment of FIGS. 1-4, the flexible sheath 24 has been shown as attached to the end surface of the proximal end 34 of the struts 38. In other embodiments, such as the embodiment shown in FIG. 5, the flexible sheath 24 has been shown as extending along the exterior of each strut 38 and attached proximate the distal end 36 of each strut 38. As also shown in FIG. 5, the accessory tube 42 extends through the ringlets 44 and also through an opening in the flexible sheath 24 to the exterior of the sheath 24. That is, the flexible sheath 24 is attached to the expandable member 22 at a location radially outside of accessory tube 42. At any point along the length of the sheath 24, the accessory tube 42 can transition through the sheath 24 be located radially outside the flexible sheath 24 and extend along the length thereof. As shown in FIG. 6, the flexible sheath 24 may also be connected to the interior of the port 32 defined by the plurality of struts 38. In this embodiment, the flexible sheath 24 is preferably located radially inside the ringlet 44 and the accessory tube 42 passing therethrough. In the embodiment of FIGS. 1-4, the accessory tube 44 may extend entirely within the sheath lumen 30 to the proximal end 26 thereof.

Figure 7:
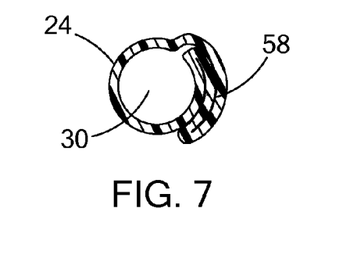
FIG. 7 is a cross-sectional view showing a delivery sheath of the medical device of FIG. 1 in its collapsed configuration.
Figure 8:
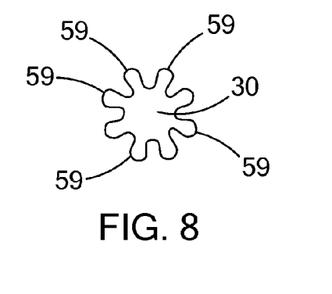
FIG. 8 is a cross-section view of another embodiment of the delivery sheath forming a portion of the medical device depicted in FIG. 1.

Turning now to FIGS. 7 and 8, the sheath 24 is also operable between a collapsed configuration in an expanded configuration. The flexible sheath 24 is preferably formed of a flexible material such as a polymer so that it is collapsible over a substantial portion of its length. That is, the sheath should be collapsible over at least the portion that is intended to be located within the body, which will include the distal portion and generally be at least half the overall length of the sheath 24. Generally, the sheath 24 folds onto itself in the collapsed configuration. As shown in FIG. 7, one collapsed configuration of the sheath 24 may include one or more large folds 58 which reduces the outer diameter of the sheath 24. As shown in FIG. 8, the sheath 24 may include a series of smaller folds 59, such as folding the sheath 24 in an accordion-style, to reduce its outer diameter in the collapsed configuration.

The flexible nature and collapsibility of the sheath 24 should be designed not only so that it may take a collapsed configuration such as those depicted, but also so that it does not restrict operability of an endoscope or other medical instrument passed through the sheath lumen 30. This can be controlled through selection of the plastic material, e.g. based on its durometer and thickness. Preferably, the sheath 24 has a thickness in the range of about 0.001 inches to about 0.1 inches, and has a sheet-like quality (in-fact, a sheet may be rolled and its edges connected to form the sheath 24). Suitable materials include fluoroplastics such as polytetrafluoroethylene (PTFE) or Teflon™, polyethylenes (high, medium or low density), polyethylene ether ketones (PEEK), polyurethanes, silicones or polyamides such as Nylon™. Most preferably, the sheath 24 is formed of low density polyurethane. The structure of the flexible sheath 24 can include multi-layer or single layer constructions with or without reinforcement wires, coils or filaments. Likewise, a polyvinylchloride (PVC) coating may also be employed for increased durability, without making the sheath 24 too rigid.

By utilizing a flexible polymer or elastomer, manipulation and operation of the endoscope 100 or other medical instrument is not compromised. Accordingly, not only can the medical device 20 facilitate operation of the medical instrument, but navigation deeper within the gastrointestinal tract via a natural bodily opening is possible. At the same time, the medical device 20 is easy to deploy and provides a secure engagement and fluidic seal with the internal bodily opening in the tissue that can prevent unwanted travel of bacteria laden fluids. Preferably, the sheath 24 has a diameter about equal to or greater than an estimated diameter of the bodily lumen (such as the esophagus 12), and collapses under a radial force that is less than the radial force anticipated from the bodily lumen. In such a configuration, the sheath 24 will not itself cause dilation or expansion of the esophagus 12 or other bodily lumen.

Figure 9:
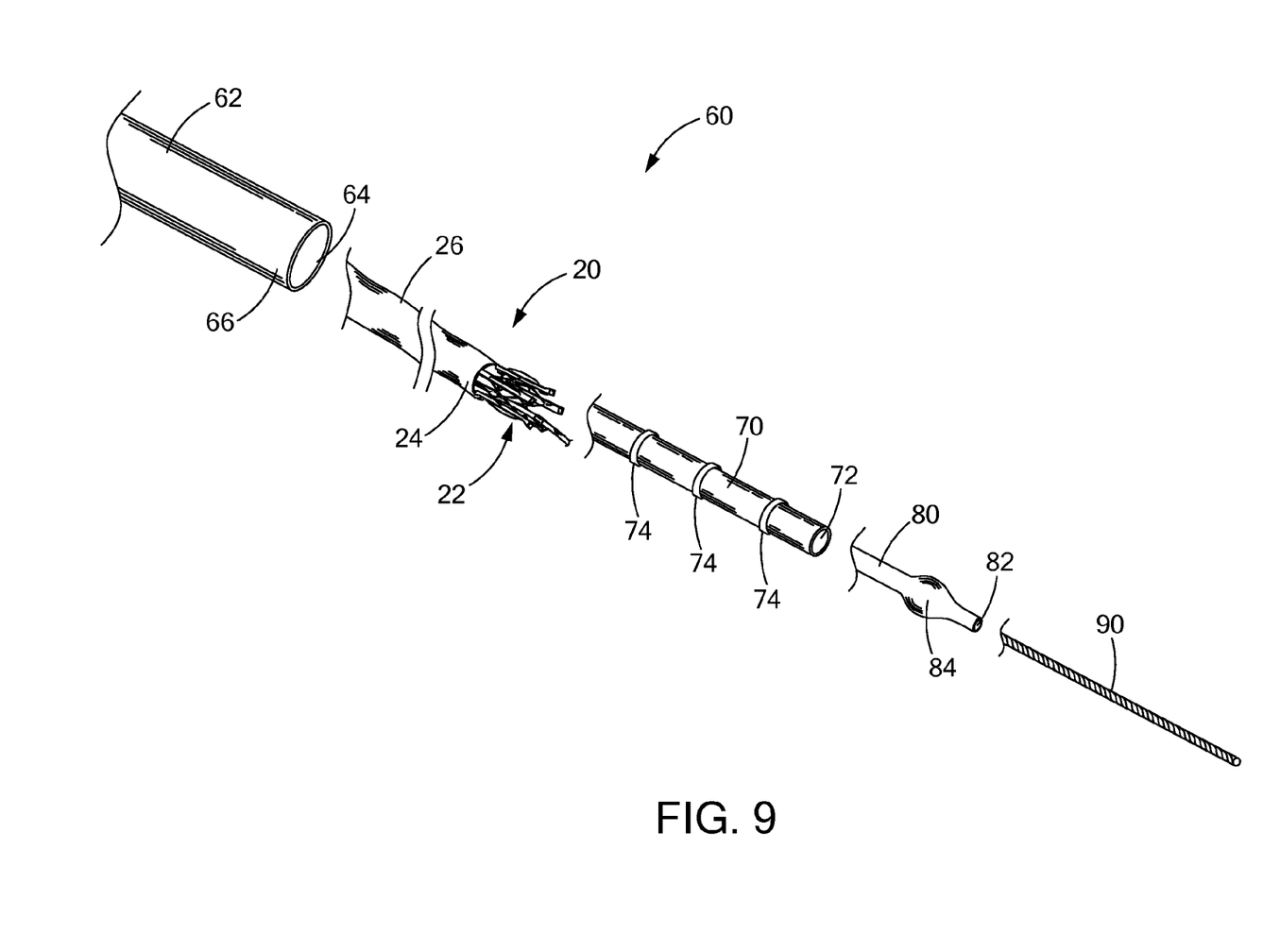
FIG. 9 is an exploded view of a medical system for deploying the medical device depicted in FIGS. 1-8, constructed in accordance with the teachings of the present invention.
Figure 10:
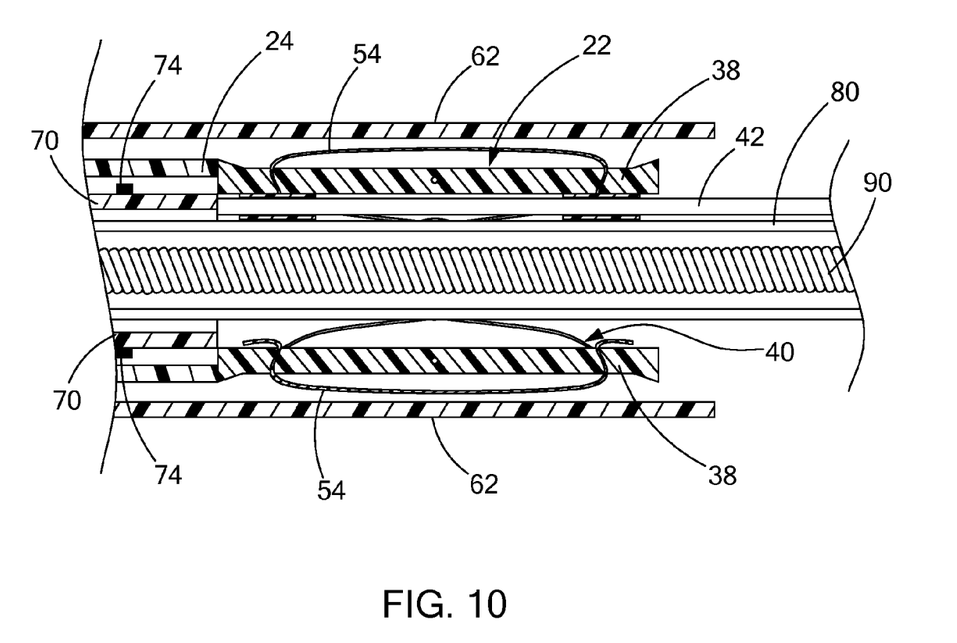
FIG. 10 is a cross-sectional view of the medical system depicted in FIG. 9.

Turning now to FIGS. 9 and 10, a medical system 60 for forming the pathway from an external orifice to a bodily opening is provided in accordance with the teachings of the present invention. The medical system 60 generally includes a medical device 20, such as those previously described, although it will be recognized that the medical system 60 may also be used with other medical devices 20 having an elongated sheath and a radially expandable member attached to a distal end of the sheath. The medical system 60 includes an outer catheter 62 defining an outer catheter lumen 64 sized to receive the medical device 20 in its collapsed configuration (shown in solid lines in FIG. 9). An inner catheter 70 is sized to be received within the sheath lumen 30 and stent lumen 32. The inner catheter 70 defines an inner catheter lumen 72. A plurality of gripping members 74 are positioned on the exterior of the inner catheter 70 and are longitudinally spaced apart. Preferably, the gripping members 74 each comprise an O-ring, gasket or other elastomeric member that may be fitted on the exterior of the inner catheter 70 by way of adhesives, bonding or simple friction fit. The gripping members 74 may have a circular cross-sectional shape, or non-circular cross-sectional shapes such as square, rectangular, triangular, oval or oblong, etc. As will be discussed in further detail herein, the gripping members 74 serve to grasp the medical device 20, and in particular the flexible sheath 24, and hold it in place while the outer catheter 62 is retracted to deploy the expandable member 22 and medical device 20.

The medical system 60 may optionally include a guiding catheter 80 which defines a guiding lumen 82 sized to receive a wire guide 90. The guiding catheter 80 may include a bulb-shaped distal end 84 that assists with loading and deploying the medical system 60, and delivering the same over the wire guide 90 to the bodily opening. Generally, the guiding catheter 80 is loaded within the inner catheter lumen 72 of the inner catheter 70. In turn, the inner catheter 70 (and guiding catheter 80) are loaded within the lumens 30, 32 of the medical device 20 in its expanded configuration (shown in dotted lines in FIG. 9). Due to the flexible and collapsible nature of the sheath 24, it will naturally take its collapsed configuration as it is positioned within the outer catheter lumen 64, although the sheath may be manually folded or otherwise manipulated as it is loaded within the outer catheter 62 to have any preferred collapsed configuration. The outer catheter 62 will be shorter than the medical device 20, inner catheter 70 and guiding catheter 80, so that their proximal ends may be grasped and pulled proximally. This causes the expandable member 22 of the medical device 20 to take its collapsed configuration and be received within the outer catheter lumen 64 of the outer catheter 62.

Figure 11:
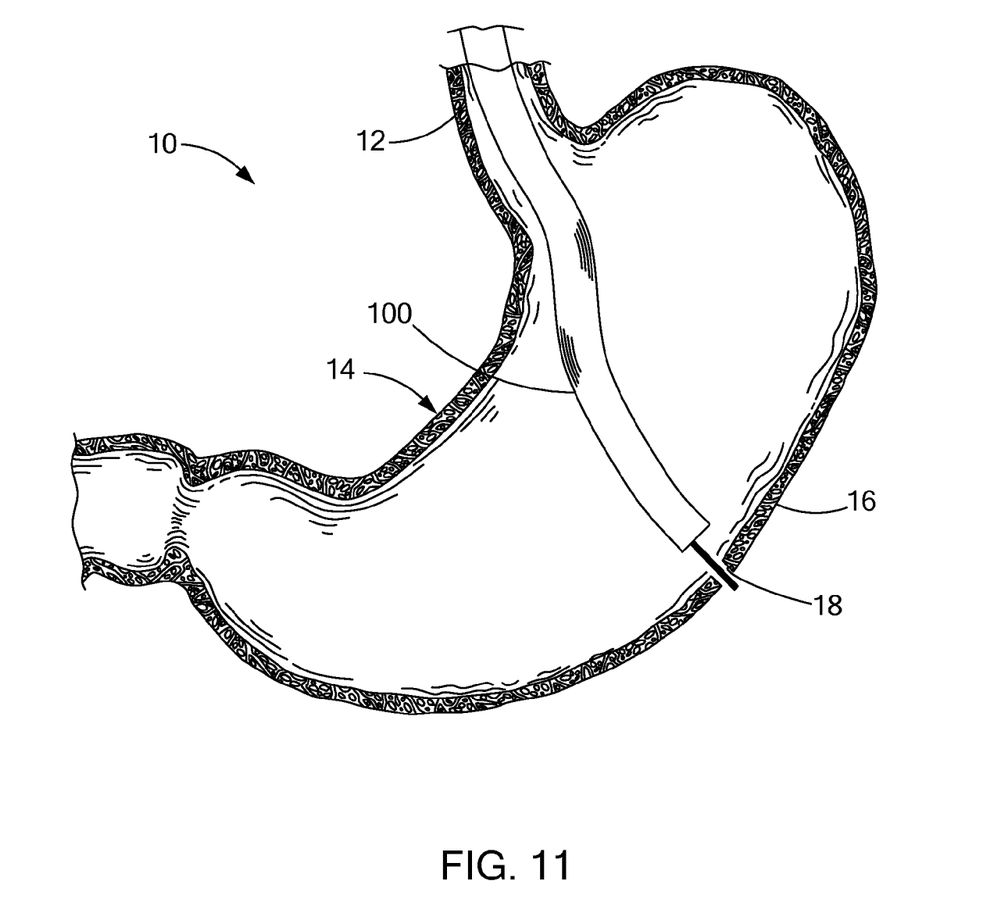
FIGS. 11-15 depict a method of employing the medical systems and devices depicted in FIGS. 1-10.
Figure 12:
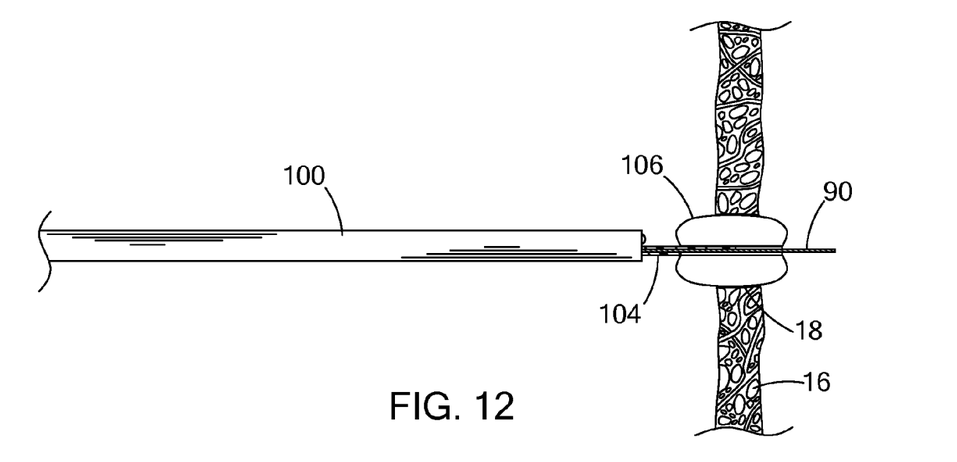

One preferred method for utilizing the medical system 60 and deploying the medical device 20 will now be described with reference to FIGS. 11-15. As shown in FIG. 11, an upper portion of the gastrointestinal tract 10, such as the esophagus 12 and stomach 14, may be accessed via the mouth (not shown). An endoscope 100 may be introduced into the stomach 14, and a cutting instrument 102 may be employed through a working channel of the endoscope 100 to form an opening 18 in the gastric tissue or gastric wall 16. As shown in FIG. 12, the wire guide 90 may be placed through the opening 18, and a dilator 104 may be introduced over the wire guide 90. Generally, the dilator 104 may include an inflation balloon 106 or other radially expandable member to enlarge the opening 18 formed in the gastric wall 16.

Figure 13:
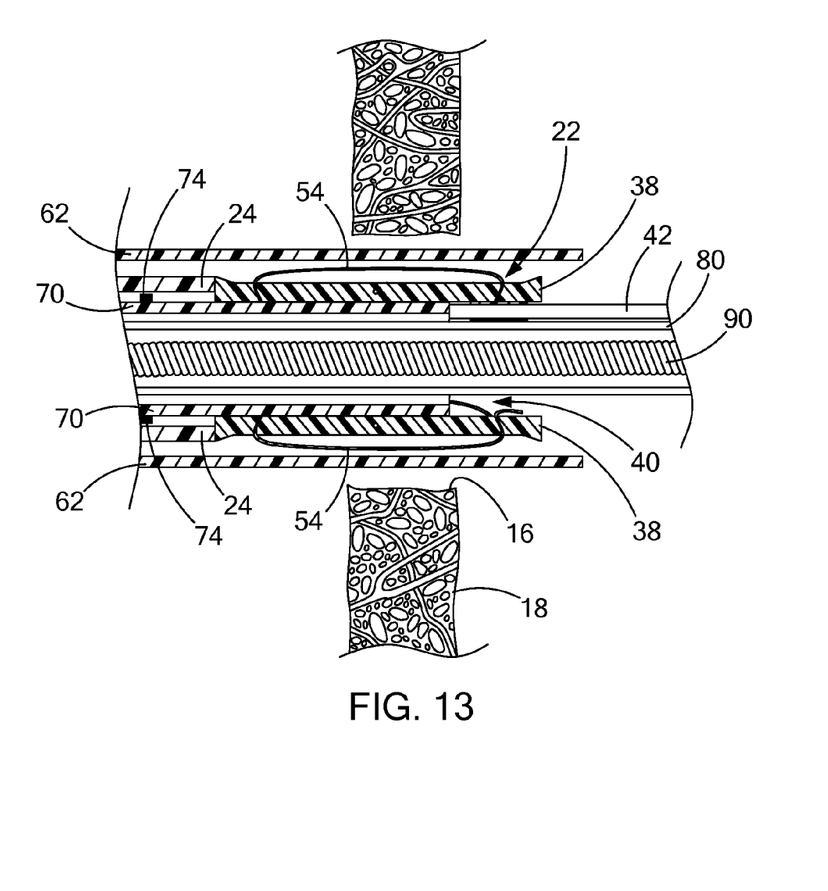

As shown in FIG. 13, the endoscope 100 and dilator 104 may be removed while leaving the wire guide 90 in place, and the medical system 60 advanced distally over the wire guide 90 to a position proximate the opening 18. More particularly, the medical system 60 is preferably positioned such that a portion of the expandable member 22 of the medical device 20 is positioned within the opening 18. To accomplish this, fluoroscopic or ultrasonic monitoring techniques may be employed, whereby the expandable member 22 may serve as the viewable element, although the outer catheter 62, the distal portion 28 of the sheath 24, or even the inner catheter 70, may include markings such as radiopaque bands or the like that facilitate visualization. Similarly, a catheter-based fiber-optic visualization system or a smaller endoscope (such as a pediatric endoscope), may be placed through the mouth and esophagus 12 into the stomach 14 (parallel to the medical system 60) for direct visualization of the medical system 60.

Figure 14:
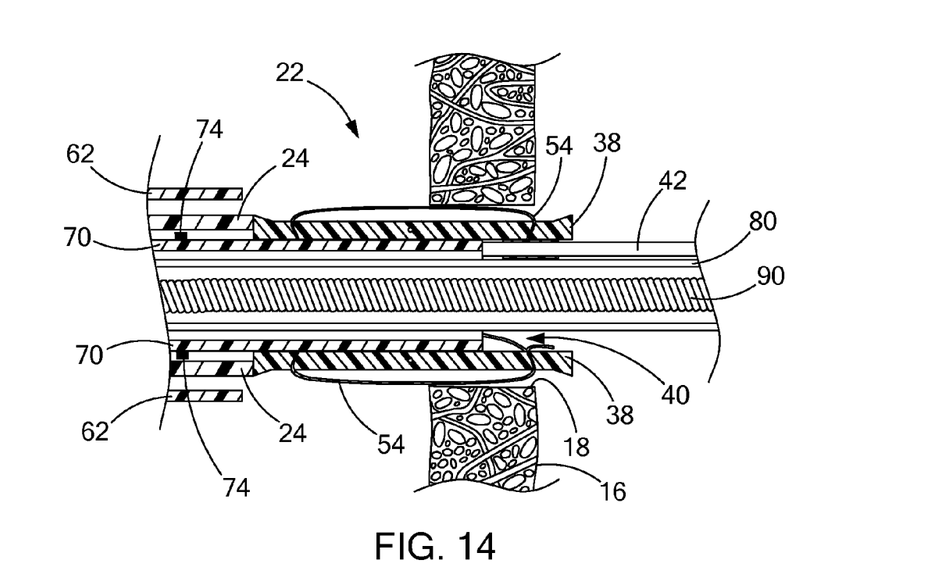
Figure 15:
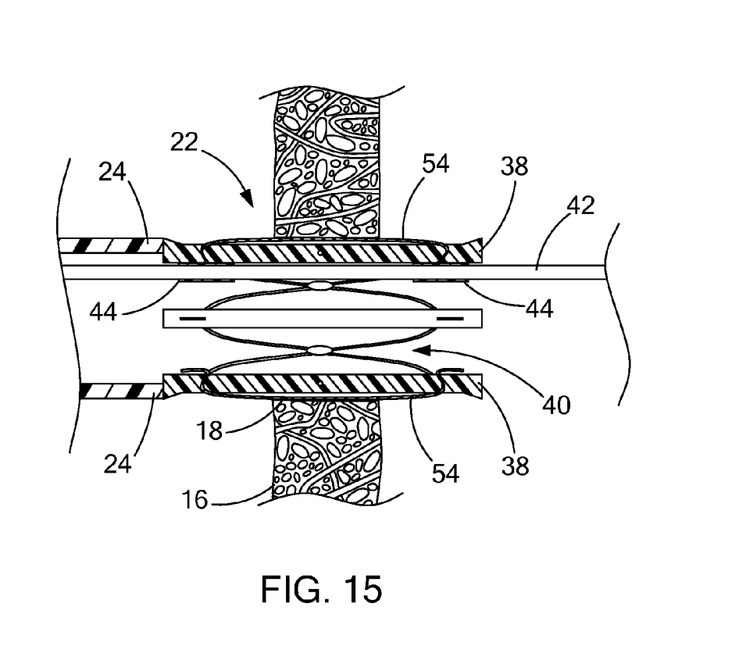

As shown in FIG. 14, the outer catheter 62 is retracted proximally relative to the inner catheter 70, which is preferably held in place. The gripping members 74 of the outer catheter 70 serve to engage the medical device 20, and in particular the sheath 24, to maintain its position and prevent it from sliding or folding or kinking due to its flexible nature, while the outer catheter 62 is retracted. As the expandable member 22 becomes exposed beyond the distal end 66 of the outer catheter 62, it will take its expanded configuration and press against the tissue 16 defining the opening 18. When the suture 15 is employed, tension on the suture 15 is maintained during delivery to hold the expandable member 22 in its collapsed configuration. Tension on the suture 15 is released to allow the wire frame 40 to cause the struts 38 to move radially outwardly and circumferentially away from each other to take the expanded configuration defining a port 32. Later, the suture 15 may again be retracted proximally to cause the expandable member 22 to take its collapsed configuration.

Through appropriate sizing of the expandable member 22, the medical device 20 will be firmly affixed to the gastric wall 16 and within the opening 18, thereby forming a port and passageway from the mouth to the bodily opening 18. The expandable member 22 exerts a radially outward force on the flexible sheath 24 and the gastric wall tissue 16 sufficient to open and maintain the opening 18, as well as affix the flexible sheath 24 and medical device 20 to the gastric wall 16. Visualization of the sutures 34 holding the expandable member 22 and sheath 24 together can assist in confirming complete deployment of the expandable member 22.

With the medical device 20 in place, the outer catheter 62 and inner catheter 70 and guiding catheter 80 may be retracted proximally and disposed of. Then, the endoscope 100 or a new endoscope may be advanced distally through the flexible sheath 24 of the medical device 20 and through the opening 18 formed in the gastric wall 16 for performing a translumenal procedure. It will be recognized by those skilled in the art that many other medical devices, in addition to or in conjunction with, an endoscope may be employed through the passageway of the medical device 20. For example, a first instrument may be passed through the port 32 defined by the expandable member 22, while a second instrument may be passed through the accessory lumen of the accessory tube 42. A surgical procedure may be used using both the first and second instruments. When it is desired to remove the medical device 24, the suture 15 (see FIG. 2) may be pulled proximally to collapse the cages of the expandable member 22, allowing the expandable member 22 and device 20 to be removed from the opening 18 in the gastric wall 16.

By utilizing a flexible sheath 24 in forming the medical device 20, manipulation and operation of the endoscope 100 or other medical instrument is not compromised. Accordingly, not only can the medical device 20 facilitate operation of the medical instrument, but navigation deeper within the gastrointestinal tract via a natural bodily opening is possible. At the same time, the medical device 20 is easy to deploy and provides a secure engagement and fluidic seal with the internal bodily opening in the tissue that can prevent unwanted travel of bacteria laden fluids. The medical devices, systems, and methods provide reliable and safe access to an internal bodily opening via an external orifice such as a natural orifice.

It will be recognized by those skilled in the art that, while the methods described above generally include placing the medical devices through an internal bodily lumen, it will be recognized that the systems, devices and methods may be used on any layer of material (e.g. fabrics, cloth, polymers, elastomers, plastics and rubber) that may not be associated with a human or animal body and a bodily lumen. For example, the systems, devices and methods can find use in laboratory and industrial settings for creating a sterile pathway through one or more layers of material that may not find application to the human or animal body.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for forming a pathway between an external orifice to a bodily opening defined by tissue of an internal bodily lumen, the medical device comprising:
   a flexible sheath having a length suitable for forming the pathway along a longitudinal axis;
   an expandable member connected to a distal portion of the sheath, the expandable member operable between a collapsed configuration and an expanded configuration;
   the expandable member including a plurality of longitudinally extending struts and a collapsible frame, the plurality of struts being circumferentially spaced apart in an annular configuration and connected to the frame, the plurality of struts moving radially and circumferentially relative to one another between the collapsed and expanded configurations;
   an elongated accessory tube defining an accessory lumen, a distal end of the accessory tube attached to the expandable member, one of the plurality of struts including a first connection ringlet and a second connection ringlet receiving the accessory tube, the second connection ringlet longitudinally spaced from the first connection ringlet.

2. The medical device of claim 1, wherein each strut is pivotally attached to the frame.

3. The medical device of claim 1, wherein each strut has distal and proximal ends that flare radially outwardly.

4. The medical device of claim 1, wherein each strut has a length equal to or greater than about 3 mm.

5. The medical device of claim 1, wherein the frame includes one or more frame members forming a serpentine shape, and wherein the plurality of struts are attached to spaced apart apexes of the serpentine shape.

6. The medical device of claim 1, further comprising a plurality of exterior wires connected to the plurality of struts and extending longitudinally along the exterior thereof for engaging the tissue of the bodily opening.

7. The medical device of claim 1, wherein the accessory tube is sized in the range of 3 French to 40 French.

8. The medical device of claim 1, wherein the accessory tube is connected to a strut.

9. The medical device of claim 1, wherein the sheath is connected to the expandable member at a radial position located outside of the accessory tube, and wherein the accessory tube passes through an opening in the sheath and extends along the exterior of the sheath.

10. The medical device of claim 1, further comprising a suture connected to the plurality struts in a manner that proximal retraction of the suture relative to the plurality of struts causes the expandable member to take its collapsed configuration.

11. The medical device of claim 10, wherein the struts include a transverse bore formed therein and sized to receive the suture.

12. The medical device of claim 11, wherein the suture is fixedly connected to at least one of the plurality of struts and slidably connected to the remainder of the struts.

13. The medical device of claim 1, wherein the plurality of struts define a port in the expanded configuration, the port sized to receive an endoscope therethrough.

14. The medical device of claim 1, wherein the sheath is collapsible over a substantial portion of its length and operable between a collapsed configuration and an expanded configuration.

15. The medical device of claim 1, wherein the sheath extends longitudinally over a proximal end of the expandable member and is attached to a distal portion of the expandable member.

16. The medical device of claim 1, wherein the connection ringlets define a central axis that extends longitudinally.

17. The medical device of claim 1, wherein the accessory tube extends entirely through the sheath from a proximal end to a distal end of the sheath.

18. A method for accessing a bodily opening defined by tissue of an internal bodily lumen via an external orifice, the method comprising:
provi­ding a medical device comprising a flexible sheath, an accessory tube, and an expandable member connected to a distal portion of the sheath, the expandable member operable between a collapsed configuration and an expanded configuration, the expandable member including a plurality of longitudinally extending struts and a wire frame, the plurality of struts being circumferentially spaced apart in an annular configuration and connected to the wire frame, the plurality of struts moving radially and circumferentially relative to one another between the collapsed and expanded configurations, the accessory tube defining an accessory lumen, a distal end of the accessory tube attached to the expandable member, one of the plurality of struts including a first connection ringlet and a second connection ringlet receiving the accessory tube, the second connection ringlet longitudinally spaced from the first connection ringlet, the accessory tube extending entirely through the sheath from a proximal end to the distal end of the sheath;
delivering the distal end of the sheath and the expandable member within the bodily opening while the expandable member is in its collapsed configuration;
operating the expandable member to its expanded configuration such that the plurality of struts form a port within the interior of the bodily opening in the bodily wall; and
passing a first instrument though the port formed by the expandable member and passing a second instrument through the accessory lumen.

19. The method of claim 18, further comprising the step of performing a surgical procedure using both the first and second instruments.

20. The method of claim 18, further comprising retracting a suture connected to the plurality of struts in a manner that proximal retraction of the suture relative to the plurality of struts causes the expandable member to take its collapsed configuration and maintaining tension on the suture during delivery, and then releasing tension to operate the expandable member to its expanded configuration.

21. The method of claim 20, further comprising the step of proximally retracting the suture to collapse the expandable member, and further comprising the step of proximally withdrawing the medical device.

* * * * *